(12) United States Patent
Libbus et al.

(10) Patent No.: US 7,630,760 B2
(45) Date of Patent: Dec. 8, 2009

(54) NEURAL STIMULATION THERAPY SYSTEM FOR ATHEROSCLEROTIC PLAQUES

(75) Inventors: Imad Libbus, St. Paul, MN (US); Julio C. Spinelli, Shoreview, MN (US); Tamara Colette Baynham, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 432 days.

(21) Appl. No.: 11/284,370

(22) Filed: Nov. 21, 2005

(65) Prior Publication Data

US 2007/0118177 A1    May 24, 2007

(51) Int. Cl.
*A61N 1/32* (2006.01)
(52) U.S. Cl. .............................. 607/2; 607/1
(58) Field of Classification Search ............... 607/1–2
See application file for complete search history.

(56) References Cited

U.S. PATENT DOCUMENTS

| | | | |
|---|---|---|---|
| 2003/0036773 | A1 | 2/2003 | Whitehurst et al. |
| 2003/0040774 | A1* | 2/2003 | Terry et al. ................. 607/2 |
| 2003/0158584 | A1 | 8/2003 | Cates et al. |
| 2004/0122477 | A1 | 6/2004 | Whitehurst et al. |
| 2004/0172075 | A1* | 9/2004 | Shafer et al. ................ 607/9 |
| 2005/0125044 | A1 | 6/2005 | Tracey |
| 2006/0178703 | A1 | 8/2006 | Huston et al. |
| 2007/0021786 | A1* | 1/2007 | Parnis et al. ................ 607/2 |
| 2007/0185535 | A1 | 8/2007 | Libbus et al. |

FOREIGN PATENT DOCUMENTS

| | | |
|---|---|---|
| WO | WO-2004110549 A2 | 12/2004 |
| WO | WO-2004110551 A2 | 12/2004 |
| WO | WO-2007058788 A1 | 5/2007 |

OTHER PUBLICATIONS

"International Search Report and Written Opinion for Application No. PCT/US2006/04286", Mailed Feb. 13, 2007.
Borovikova, L. V., et al., "Role of vagus nerve signaling in CNI-1493-mediated suppression of acute inflammation", *Auton Neurosci.*, 85(1-3), (Dec. 2000),141-7.

(Continued)

*Primary Examiner*—Carl H Layno
*Assistant Examiner*—Deborah Malamud
(74) *Attorney, Agent, or Firm*—Schwegman, Lundberg & Woessner, P.A.

(57) ABSTRACT

A neural stimulation therapy system for atherosclerotic plaques is provided. One aspect of this disclosure relates to a medical device for applying neural stimulation therapy for atherosclerotic plaques. The device includes a neural stimulator adapted to deliver an electrical signal through at least one electrode to an autonomic neural target. The device also includes a controller to control the neural stimulator to provide a therapy for atherosclerotic plaques. The device is external to a human body in an embodiment, and includes an implantable medical device (IMD) in various embodiments. According to an embodiment, the device includes a neural stimulation lead connected to the neural stimulator. The neural stimulator delivers electrical signals with waveform parameters based on sensed arterial blockage levels, according to various embodiments. Other aspects and embodiments are provided herein.

43 Claims, 6 Drawing Sheets

OTHER PUBLICATIONS

Borovikova, L. V., "Vagus nerve stimulation attenuates the systemic inflammatory response to endotoxin", *Nature*, 405(6785), (May 25, 2000),458-62.

Chekanov, V. S., "Pathologic and histologic results of electrical impulses in a rabbit model of atherosclerosis: 24-hour versus 8-hour regimen.", *J Vasc Surg.*, 35(3), (Mar. 2002),554-62.

Chekanov, V., et al., "Slowed progression or elimination of atherosclerosis by low-frequency electrical impulses", *J Card Surg.*, 18(1), (Jan.-Feb. 2003),47-58.

Lathrop, D. A., "On the neural connection", *Journal of Cardiovascular Electrophysiology*, vol. 12, No. 7 (Jul. 2001),841-844.

Tracey, K. J., "The inflammatory reflex", *Nature*, 420(6917), (Dec. 19-26, 2002),853-9.

* cited by examiner

NEURAL STIMULATION THERAPY SYSTEM FOR ATHEROSCLEROTIC PLAQUES

TECHNICAL FIELD

This disclosure relates generally to medical devices and, more particularly, to systems and methods of neural stimulation therapy for atherosclerotic plaques.

BACKGROUND

Neural stimulation has been the subject of a number of studies and has been proposed for several therapies. The autonomic system controls physiological activities of the body and the imbalance of autonomic tone is related to many diseases and conditions. Reduced autonomic balance (increase in sympathetic and decrease in parasympathetic cardiac tone) during heart failure has been shown to be associated with left ventricular dysfunction and increased mortality. Sympathetic inhibition, as well as parasympathetic activation, have been associated with reduced arrhythmia vulnerability following a myocardial infarction. Vagus nerve stimulation has been proposed to treat sleep disorders, gastrointestinal motility, eating disorders, obesity, anorexia, gastrointestinal tract disorders, hypertension, coma, and epilepsy. Direct electrical stimulation of parasympathetic nerves can activate the baroreflex, inducing a reduction of sympathetic nerve activity and reducing blood pressure by decreasing vascular resistance. Direct stimulation of the vagal parasympathetic fibers has been shown to reduce heart rate via the sympathetic nervous system. In addition, some research indicates that chronic stimulation of the vagus nerve may be of protective myocardial benefit following cardiac ischemic insult.

Atherosclerosis begins with the appearance of cholesterol-laden macrophages (foam cells) in the intima of an artery. Smooth muscle cells respond to the presence of lipid by proliferating, under the influence of platelet factors. A plaque forms at the site, consisting of smooth muscle cells, leukocytes, and further deposition of lipid; in time the plaque becomes fibrotic and may calcify. Expansion of an atherosclerotic plaque leads to gradually increasing obstruction of the artery and ischemia of tissues supplied by it. Ulceration, thrombosis, or embolization of a plaque, or intimal hemorrhage and dissection, can cause more acute and severe impairment of blood flow, with the risk of infarction.

Treatment of atherosclerosis includes balloon stretching, laser ablation, or surgical removal of plaques, and various bypass and grafting procedures. Current preventive measures for atherosclerosis include regular vigorous exercise, a diet low in fat and cholesterol, maintenance of a healthful weight, avoidance of tobacco, and use of pharmacologic agents as indicated.

SUMMARY

Disclosed herein, among other things, is a medical device for applying neural stimulation therapy for atherosclerotic plaques. The device includes a neural stimulator adapted to deliver an electrical signal through at least one electrode to an autonomic neural target. The device also includes a controller to control the neural stimulator to provide a therapy for atherosclerotic plaques. The device is external to a human body in an embodiment, and includes an implantable medical device (IMD) in various embodiments. According to an embodiment, the device includes a neural stimulation lead connected to the neural stimulator. The neural stimulator delivers electrical signals with waveform parameters based on sensed arterial blockage levels, according to various embodiments.

Another aspect of the device includes a sensing circuit to receive sensed signals representative of blood flow in a vessel to determine extent of blockage. The device also includes a neural stimulator adapted to deliver an electrical signal through at least one electrode to an autonomic neural target. The device further includes a controller to communicate with the sensing circuit and to control the neural stimulator to provide a therapy for atherosclerotic plaques.

One aspect of this disclosure relates to a system for applying neural stimulation therapy for atherosclerotic plaques. The system includes at least one neural stimulation lead having a proximal portion and a distal portion. The system also includes a plurality of electrodes along the distal portion of the at least one lead. In addition, the system includes a medical device coupled to the proximal portion of the at least one lead. The device includes a neural stimulator adapted to deliver an electrical signal through at least one electrode to an autonomic neural target. The device also includes a controller to control the neural stimulator to provide a therapy for atherosclerotic plaques. The neural stimulator delivers electrical signals with waveform parameters based on sensed arterial blockage levels, according to various embodiments.

Another aspect of the system includes means for monitoring blood pressure in a vessel to determine extent of blockage. The system also includes means for applying neural stimulation based on the extent of blockage, where the stimulation adapted to provide a therapy for atherosclerotic plaques. According to an embodiment, the system also includes means for applying cardiac rhythm management therapy.

One aspect of this disclosure relates to a method of neural stimulation therapy for atherosclerotic plaques. The method includes monitoring blood flow in a vessel to determine extent of blockage. The method also includes applying neural stimulation based on the extent of blockage, the stimulation adapted to provide a therapy for atherosclerotic plaques. According to an embodiment, the method also includes monitoring blood pressure in a vessel to determine extent of blockage. The method further includes applying cardiac rhythm management therapy in conjunction with neural stimulation therapy, according to various embodiments.

This Summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

DETAILED DESCRIPTION

The following detailed description refers to the accompanying drawings which show, by way of illustration, specific aspects and embodiments in which the present invention may be practiced. The various embodiments are not necessarily mutually exclusive, as aspects of one embodiment can be combined with aspects of another embodiment. These embodiments are described in sufficient detail to enable those skilled in the art to practice the invention. Other embodiments may be utilized and structural, logical, and electrical changes may be made without departing from the scope of the present invention.

Neural Stimulation

A brief discussion of the physiology related to neurology is provided to assist the reader with understanding this disclosure. The automatic nervous system (ANS) regulates "involuntary" organs. The ANS includes the sympathetic nervous system and the parasympathetic nervous system. The sympathetic nervous system is affiliated with stress and the "fight or flight response" to emergencies. The parasympathetic nervous system is affiliated with relaxation and the "rest and digest response." The ANS maintains normal internal function and works with the somatic nervous system. Autonomic balance reflects the relationship between parasympathetic and sympathetic activity. A change in autonomic balance is reflected in changes in heart rate, heart rhythm, contractility, remodeling, inflammation and blood pressure. Changes in autonomic balance can also be seen in other physiological changes, such as changes in abdominal pain, appetite, stamina, emotions, personality, muscle tone, sleep, and allergies, for example.

An example of neural stimulation is baroreflex stimulation. Baroreflex is a reflex triggered by stimulation of a baroreceptor. A baroreceptor includes any sensor of pressure changes, such as sensory nerve endings in the wall of the auricles of the heart, vena cava, aortic arch and carotid sinus, that is sensitive to stretching of the wall resulting from increased pressure from within, and that functions as the receptor of the central reflex mechanism that tends to reduce that pressure. Afferent nerve trunks, such as the vagus, aortic and carotid nerves, leading from the sensory nerve endings also form part of a baroreflex pathway. Stimulating a baroreflex pathway and/or baroreceptors inhibits sympathetic nerve activity, stimulates the parasympathetic nervous system and reduces systemic arterial pressure by decreasing peripheral vascular resistance and cardiac contractility. Baroreceptors are naturally stimulated by internal pressure and the stretching of vessel wall (e.g. arterial wall). Neural stimulation of other neural targets is within the scope of the present disclosure, including stimulation of efferent and afferent pathways for parasympathetic and sympathetic nerves.

A neural stimulation lead is a lead for delivering neural stimulation therapy, and can be placed in a number of appropriate locations. For example, various lead embodiments to stimulate a baroreflex are expandable, and are adapted to be placed in the pulmonary artery in the proximity of a high concentration of baroreceptors. Various lead embodiments are adapted to stimulate nerve endings in cardiac fat pads. Some lead embodiments are transvascular leads placed proximal to a cardiac fat pad. Some lead embodiments place an epicardial lead in a cardiac fat pad. Various lead embodiments include a cuff electrode adapted to be placed around a nerve, such as the aortic, carotid or vagus nerve. A nerve cuff refers to any lead configuration that is placed around a nerve trunk, including configurations placed around a sheath containing a nerve trunk. Some lead embodiments include a transvascular lead placed proximal to a nerve, such as the vagus, aortic, or carotid nerve. Other leads can be placed in other neural stimulation and neural sensing locations to perform baroreflex or other therapy.

Atherosclerosis

In general, atherosclerosis is a cardiovascular disease in which the vessel wall is remodeled, compromising the lumen of the vessel. The atherosclerotic remodeling process involves accumulation of cells, both smooth muscle cells and monocyte/macrophage inflammatory cells, in the intima of the vessel wall. These cells take up lipid, likely from the circulation, to form a mature atherosclerotic lesion. Although the formation of these lesions is a chronic process, occurring over decades of an adult human life, the majority of the morbidity associated with atherosclerosis occurs when a lesion ruptures, releasing thrombogenic debris that rapidly occludes the artery. When such an acute event occurs in the coronary artery, myocardial infarction can ensue, and in the worst case, can result in death.

Atherosclerosis is a serious health problem affecting millions of humans. Preventing the formation and rupture of atherosclerotic plaque would be of significant clinical benefit.

The present system provides a medical device for applying neural stimulation therapy to patients with atherosclerosis. In various embodiments, systemic or local neural stimulation is applied intermittently to inhibit inflammatory response, preventing or reducing plaque formation and increasing the stability of existing plaques, thereby decreasing the severity of atherosclerosis.

Medical Devices

Figure 1A:
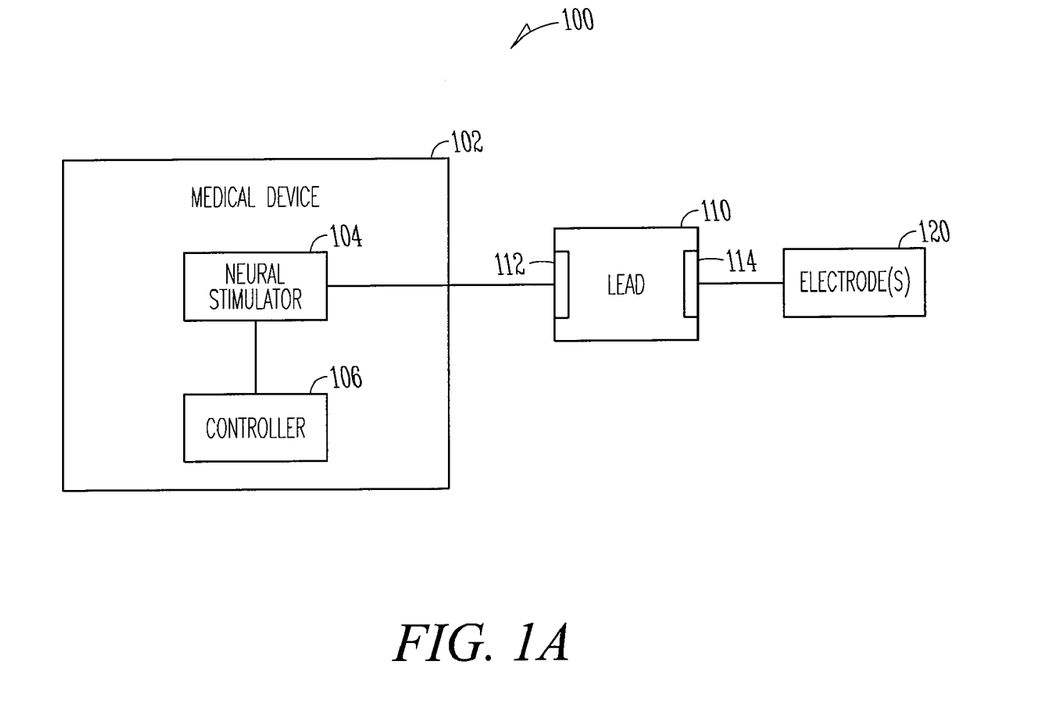
FIG. 1A illustrates a system for applying neural stimulation therapy for atherosclerotic plaques including a medical device, according to one embodiment.

FIG. 1A illustrates a system for applying neural stimulation therapy for atherosclerotic plaques including a medical device, according to one embodiment. The system 100 includes at least one neural stimulation lead 110 having a proximal portion 112 and a distal portion 114. The system also includes a plurality of electrodes 120 along the distal portion of the at least one lead. In addition, the system includes a medical device 102 coupled to the proximal portion of the at least one lead. The device includes a neural stimulator 104 adapted to deliver an electrical signal through at least one electrode to an autonomic neural target. The device also includes a controller 106 to control the neural stimulator to provide a therapy for atherosclerotic plaques. The neural stimulator delivers electrical signals with waveform parameters based on sensed arterial blockage levels, according to various embodiments. Examples of waveform parameters which can be modulated based on sensed arterial blockage levels include frequency, amplitude and phase of the waveform. According to various embodiments, the stimulation is applied to an autonomic parasympathetic target to attenuate systemic inflammation associated with atherosclerosis.

Figure 1B:
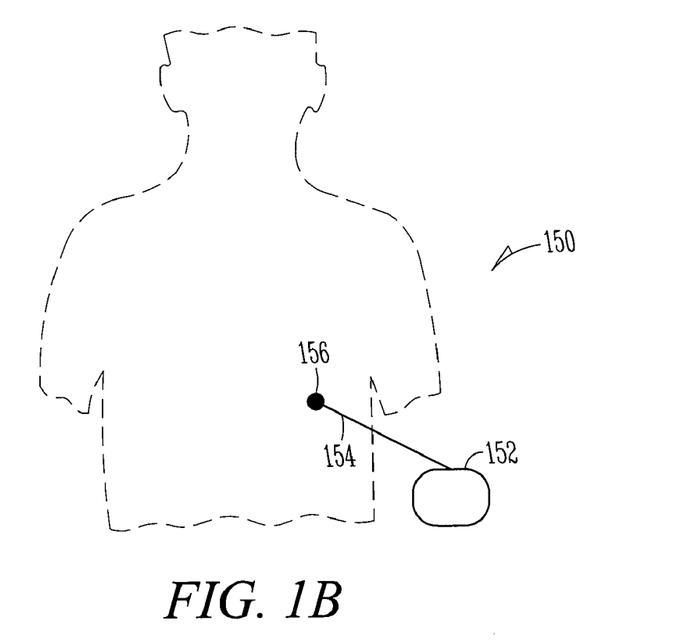
FIG. 1B illustrates a system for applying neural stimulation therapy for atherosclerotic plaques including an external medical device, according to one embodiment.

FIG. 1B illustrates a system for applying neural stimulation therapy for atherosclerotic plaques including an external medical device 152, according to one embodiment. In this embodiment, neural stimulation therapy is delivered from the device 152 external to a human body 150 transcutaneously to provide therapy for atherosclerotic plaques. An external lead 154 and electrode 156 are included in an embodiment.

Figure 1C:
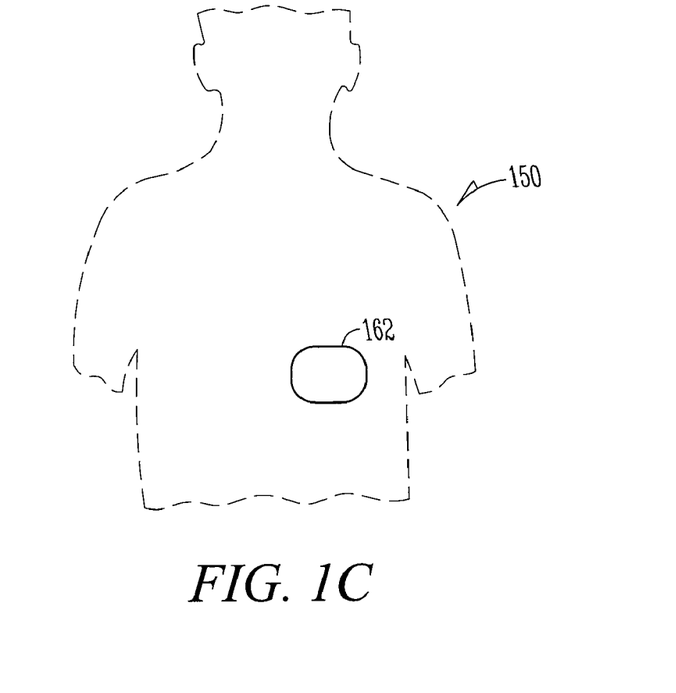
FIG. 1C illustrates a system for applying neural stimulation therapy for atherosclerotic plaques including an implantable medical device (IMD), according to one embodiment.

FIG. 1C illustrates a system for applying neural stimulation therapy for atherosclerotic plaques including an implantable medical device (IMD) 162, according to one embodiment. In this embodiment, neural stimulation therapy is delivered from the device 162 implanted in a human body 150.

Referring to FIG. 1A, the plurality of electrodes 120 includes an expandable, stent-type electrode adapted to provide mechanical and electrical anti-atherosclerotic therapy according to an embodiment. For example, the stent-type electrode can be used to provide structural support during electrical stimulation to target local inflammation. The device 102 includes a pacemaker, according to various embodiments. Thus, neural stimulation therapy can be delivered in conjunction with cardiac pacing, allowing for maintained cardiac output if autonomic stimulation has cardiac effect, such as bradycardia or asystole.

The neural stimulator 104 delivers electrical signals intermittently, according to various embodiments. For example, the electrical signals may be delivered in bursts for several seconds, with several seconds delay between bursts. The bursts and delays may be of the same or different duration, and can be adjusted by the controller based on sensor feedback, according to various embodiments.

In various embodiments, the at least one lead 110 includes a lead with an expandable portion. In one embodiment, the lead with the expandable portion is placed in a pulmonary artery in proximity of a high concentration of baroreceptors. In various embodiments, the at least one lead 110 includes a transvascular lead. In one embodiment, the transvascular lead is placed proximal to a cardiac fat pad. The transvascular lead is placed proximal to an aortic nerve, in an embodiment. In an embodiment, the transvascular lead is placed proximal to a carotid nerve. The transvascular lead is placed proximal to a vagus nerve, in an embodiment. In various embodiments, the at least one lead 110 includes an epicardial lead. The epicardial lead is placed in a cardiac fat pad, in one embodiment.

Neural stimulation lead placement may be determined by the site of atherosclerosis. For example, in the case of coronary artery disease, local cardiac autonomic therapy may be provided via stimulation of cardiac branches of the vagus nerve or cardiac fat pads. Alternatively, the neural stimulation lead could be placed directly in the vicinity of an existing atherosclerotic plaque.

In various embodiments, the plurality of electrodes 120 includes at least one cuff electrode. The cuff electrode is placed around an aortic nerve, in one embodiment. In an embodiment, the cuff electrode is placed around a carotid nerve. The cuff electrode is placed around a vagus nerve, in one embodiment. According to various embodiments, the plurality of electrodes includes at least one satellite electrode having its own power supply and which is capable of wireless communication with the medical device. An example of a satellite electrode is described in U.S. patent application Ser. No. 10/079,056, filed on Feb. 19, 2002, assigned to Cardiac Pacemaker, Inc. The plurality of electrodes includes at least one electrode on or in the medical device itself, according to various embodiments.

Another aspect of the system includes means for monitoring blood pressure in a vessel to determine extent of blockage. According to various embodiments, monitoring means include sensors as discussed in FIG. 2 below, among others. The system also includes means for applying neural stimulation based on the extent of blockage, where the stimulation adapted to provide a therapy for atherosclerotic plaques. According to various embodiments, stimulating means include, for example, a neural stimulator as discussed in FIG. 1A above, among others. According to an embodiment, the means for applying neural stimulation includes at least one lead. The lead or leads are placed in a location known to activate the parasympathetic nervous system, in an embodiment. The lead or leads are placed in proximity to a site of atherosclerosis, in another embodiment. According to various embodiments, therapy for atherosclerotic plaques includes electrically stimulating an autonomic neural target to reduce inflammatory response of atherosclerosis, prevent plaque formation, and promote stability of existing plaque.

According to an embodiment, the system also includes means for applying cardiac rhythm management (CRM) therapy. According to various embodiments, CRM therapy means includes a pacemaker or pulse generator as discussed in FIG. 3 below, among others. In an embodiment, the system also includes means for monitoring blood flow in a vessel to determine extent of blockage.

Figure 2:
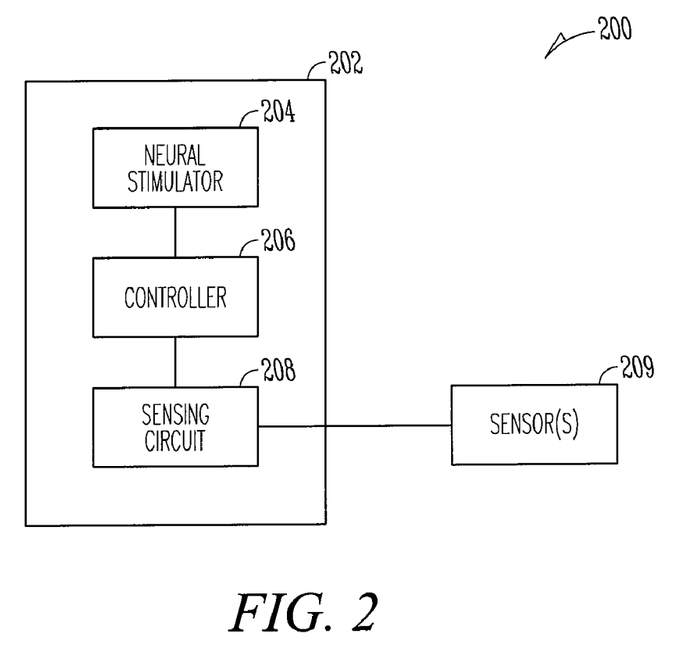
FIG. 2 illustrates a system for applying neural stimulation therapy for atherosclerotic plaques including a sensing circuit, according to one embodiment.

FIG. 2 illustrates a system for applying neural stimulation therapy for atherosclerotic plaques including a sensing circuit, according to one embodiment. The depicted system 200 includes a medical device 202 and at least one sensor 209. The device 202 includes a sensing circuit 208 to receive sensed signals representative of blood flow in a vessel to determine extent of blockage. The device also includes a neural stimulator 204 adapted to deliver an electrical signal through at least one electrode to an autonomic neural target. The device further includes a controller 206 to communicate with the sensing circuit and to control the neural stimulator to provide a therapy for atherosclerotic plaques.

According to various embodiments, the sensor 209 includes a mechanical sensor to detect blood flow. According to various embodiments, the sensor includes a device to sense blood pressure. The sensor allows therapy application to be controlled with a closed-loop feedback system. In an embodiment, the sensor includes a Doppler flow meter placed at or near an appropriate vessel to transvascularly monitor blood flow and allow the controller to modulate therapy based on the extent of arterial blockage. The neural stimulator is adapted to connect to at least one neural stimulation lead, according to an embodiment.

Figure 3:
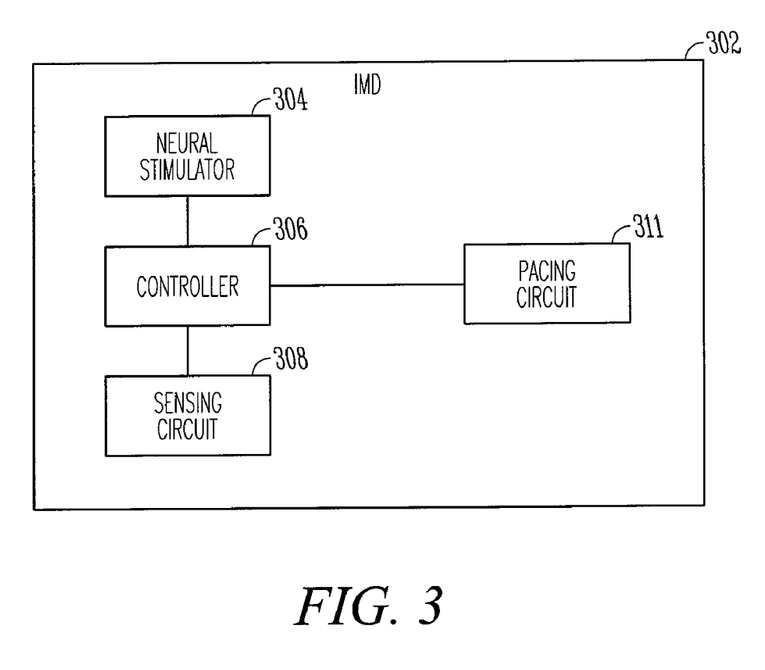
FIG. 3 illustrates an IMD for applying neural stimulation therapy for atherosclerotic plaques including a pacing circuit, according to one embodiment.

FIG. 3 illustrates an IMD for applying neural stimulation therapy for atherosclerotic plaques including a pacing circuit, according to one embodiment. The IMD 302 includes a sensing circuit 308 to receive sensed signals representative of blood flow in a vessel to determine extent of blockage. The device also includes a neural stimulator 304 adapted to deliver an electrical signal through at least one electrode to an autonomic neural target. The device further includes a controller 306 to communicate with the sensing circuit and to control the neural stimulator to provide a therapy for atherosclerotic plaques. A pacing circuit 311 is included in the IMD in various embodiments. The pacing circuit is adapted to provide cardiac rhythm management therapy in conjunction with the described neural stimulation therapy.

Combining Therapy for Atherosclerotic Plaques with Cardiac Conditioning

The IMD 302 depicted in FIG. 3 can be implanted in patients with artery disease. These patients likely have an elevated risk for a myocardial infarction. According to various embodiments, the IMD is adapted to deliver therapy for atherosclerotic plaques (as described above) and is also adapted to deliver cardiac preconditioning therapy. The IMD delivers atherosclerosis therapy in combination with cardiac preconditioning therapy, according to an embodiment. According to various embodiments, the IMD begins applying preconditioning therapy when sensed arterial blockage reaches a predefined threshold. In addition, atherosclerosis therapy and preconditioning therapy are independently delivered and controlled within the IMD 302, according to an embodiment.

Cardiac preconditioning is defined herein as intermittent pacing or neural stimulation to provide prophylactic protection from potential subsequent ischemia or ischemia/reperfusion injury. Types of pacing used in cardiac preconditioning include intermittent ventricular pacing or intermittent modulation of ventricular pacing. Preconditioning has two phases: an early phase lasting between 5 minutes and 2 hours after an applied stimulus; and a late phase (or second window of protection) lasting between 24 hours and 3 days after the stimulus. According to an embodiment, a sequence of pacing for maintained preconditioning includes 1 to 4 cycles of 3 to 20 minutes of pacing applied every 1 to 3 days. Cardiac preconditioning may reduce infarct size and contribute to the prevention and attenuation of heart failure.

According to various embodiments, the device is adapted to deliver therapy for atherosclerotic plaques and is also adapted to deliver cardiac postconditioning therapy. The device delivers atherosclerosis therapy in combination with cardiac postconditioning therapy, according to an embodiment. According to various embodiments, the IMD begins applying postconditioning therapy when sensed arterial blockage reaches a predefined threshold. In addition, atherosclerosis therapy and postconditioning therapy are independently delivered and controlled within the IMD 302, according to an embodiment.

Cardiac postconditioning is defined herein as intermittent pacing or neural stimulation after ischemic injury to protect the heart against further damage from ischemia/reperfusion injury. Short intervals of ischemia during the reperfusion phase can provide a significant reduction in subsequent infarct size. According to an embodiment, a sequence of pacing for postconditioning commences no later than 2 minutes after the institution of reperfusion and includes 4 to 10 cycles of 10 seconds to 1 minute of pacing.

System for Applying Neural Stimulation Therapy for Atherosclerotic Plaques

Figure 4:
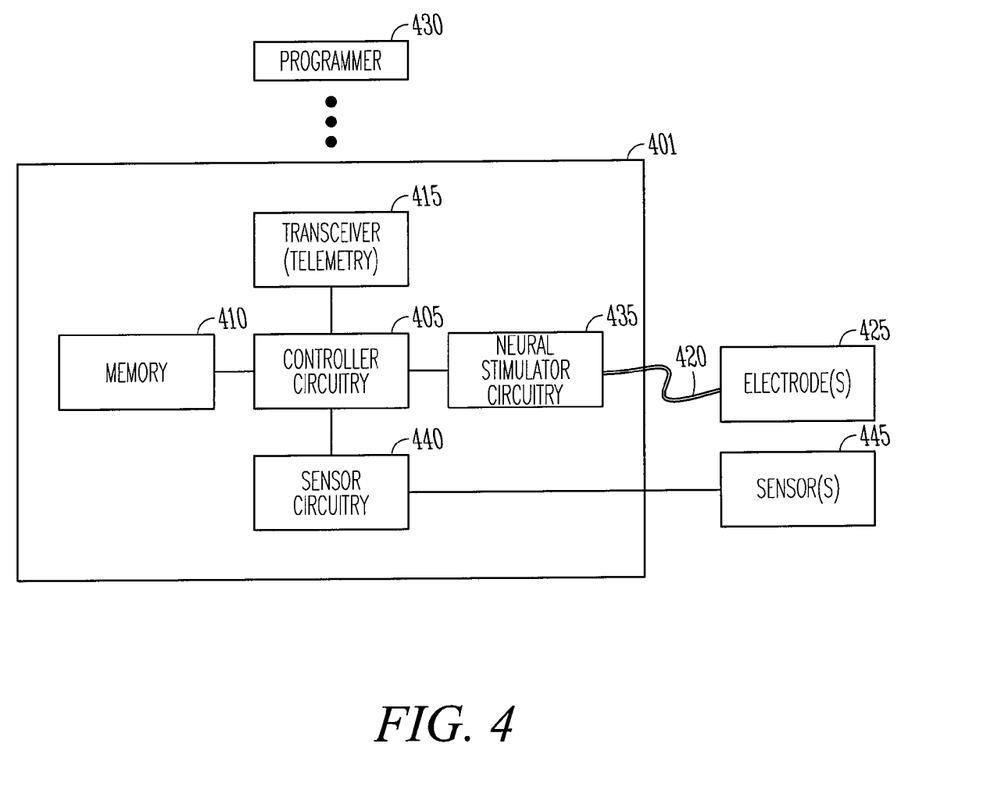
FIG. 4 is a schematic illustration of an implantable system for neural stimulation therapy for atherosclerotic plaques, according to one embodiment.

FIG. 4 is a schematic illustration of an implantable system for neural stimulation therapy for atherosclerotic plaques, according to one embodiment. The system includes an IMD 401, an electrical lead 420 coupled to the IMD 401, and at least one electrode 425. The IMD includes a controller circuit 405, a memory circuit 410, a telemetry circuit 415, and a neural stimulation circuit 435. The controller circuit 405 is operable on instructions stored in the memory circuit to deliver an electrical neural stimulation therapy. Therapy is delivered by the neural stimulation circuit 435 through the lead 420 and the electrode(s) 425. The telemetry circuit 415 allows communication with an external programmer 430. The programmer 430 can be used to adjust the programmed therapy provided by the IMD 401, and the IMD can report device data (such as battery and lead resistance) and therapy data (such as sense and stimulation data) to the programmer using radio telemetry, for example. According to various embodiments, the IMD 401 senses one or more physiological parameters and delivers neural stimulation therapy as disclosed in the method depicted in FIG. 6, described below. The illustrated system also includes sensor circuitry 440 that is coupled to at least one sensor 445. The controller circuit 405 processes sensor data from the sensor circuitry and delivers a therapy responsive to the sensor data.

Figure 5:
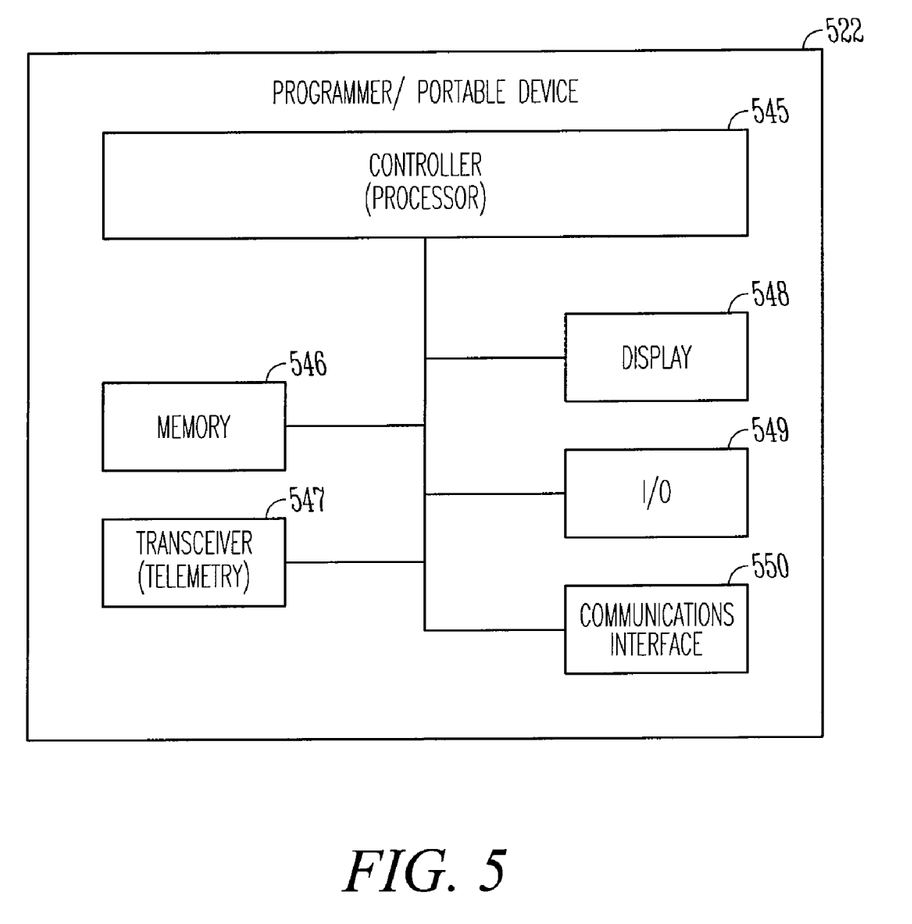
FIG. 5 illustrates a programmer such as illustrated in the system of FIG. 4 or other external device to communicate with the implantable medical device(s), according to one embodiment.

FIG. 5 illustrates a programmer 522, such as the programmer 430 illustrated in the system of FIG. 4 or other external device to communicate with the implantable medical device(s), according to one embodiment. An example of another external device includes Personal Digital Assistants (PDAs) or personal laptop and desktop computers in an Advanced Patient Management (APM) system. The illustrated device 522 includes controller circuitry 545 and a memory 546. The controller circuitry 545 is capable of being implemented using hardware, software, and combinations of hardware and software. For example, according to various embodiments, the controller circuitry 545 includes a processor to perform instructions embedded in the memory 546 to perform a number of functions, including communicating data and/or programming instructions to the implantable devices. The illustrated device 522 further includes a transceiver 547 and associated circuitry for use to communicate with an implantable device. Various embodiments have wireless communication capabilities. For example, various embodiments of the transceiver 547 and associated circuitry include a telemetry coil for use to wirelessly communicate with an implantable device. The illustrated device 522 further includes a display 548, input/output (I/O) devices 549 such as a keyboard or mouse/pointer, and a communications interface 550 for use to communicate with other devices, such as over a communication network.

Method of Neural Stimulation Therapy for Atherosclerotic Plaques

Figure 6:
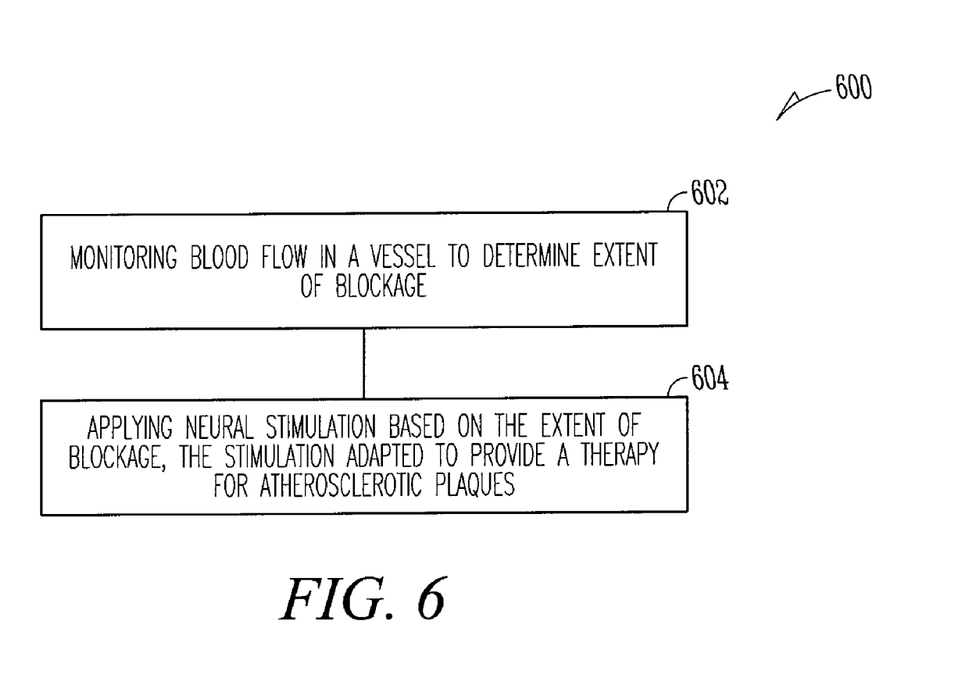
FIG. 6 illustrates a flow diagram of a method of neural stimulation therapy for atherosclerotic plaques, according to one embodiment.

FIG. 6 illustrates a flow diagram of a method of neural stimulation therapy for atherosclerotic plaques, according to one embodiment. The method 600 includes monitoring blood flow in a vessel to determine extent of blockage, at 602. The method also includes applying neural stimulation based on the extent of blockage, the stimulation adapted to provide a therapy for atherosclerotic plaques, at 604. According to an embodiment, the method also includes monitoring blood pressure in a vessel to determine extent of blockage. The method further includes applying cardiac rhythm management therapy in conjunction with neural stimulation therapy, according to various embodiments.

According to an embodiment, the method also includes applying cardiac preconditioning therapy in conjunction with neural stimulation therapy. The method further includes applying cardiac postconditioning therapy in conjunction with neural stimulation therapy, in an embodiment. According to various embodiments, preconditioning therapy is applied when the extent of blockage reaches a predefined threshold. Postconditioning therapy is applied when the extent of blockage reaches a predefined threshold, according to an embodiment.

According to various embodiments, applying neural stimulation includes applying electrical signals proximate a site of atherosclerosis. Applying neural stimulation includes stimulating an autonomic neural target, according to various embodiments. According to various embodiments, providing therapy for atherosclerotic plaques includes electrically stimulating an autonomic neural target to reduce inflammatory response of atherosclerosis, prevent plaque formation, and promote stability of existing plaque.

One of ordinary skill in the art will understand that, the modules and other circuitry shown and described herein can be implemented using software, hardware, and combinations of software and hardware. As such, the illustrated modules and circuitry are intended to encompass software implementations, hardware implementations, and software and hardware implementations.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof, can be combined. In various embodiments, the methods provided above are implemented as a computer data signal embodied in a carrier wave or propagated signal, that represents a sequence of instructions which, when executed by a processor cause the processor to perform the respective method. In various embodiments, methods provided above are implemented as a set of instructions contained on a computer-accessible medium capable of directing a processor to perform the respective method. In various embodiments, the medium is a magnetic medium, an electronic medium, or an optical medium.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments as well as combinations of portions of the above embodiments in other embodiments will be apparent to those of skill in the art upon reviewing the above description. The scope of the present subject matter should be determined with reference to the appended claims, along with the full scope of equivalents to which such claims are entitled.

What is claimed is:

1. A medical device, comprising:
   at least one neural stimulation electrode adapted to be placed proximate to a site of atherosclerosis to enable stimulation of the site of atherosclerosis or stimulation of a peripheral neural pathway that is proximate to and that innervates the site of atherosclerosis;
   a neural stimulator adapted to deliver an electrical signal through the at least one electrode to stimulate the site of atherosclerosis or to stimulate the peripheral neural pathway proximate to the site of atherosclerosis to provide local therapy that reduces an inflammatory response at the site of atherosclerosis; and
   a programmed controller, wherein the controller is programmed with a therapy for atherosclerotic plaques to control the neural stimulator to intermittently deliver stimulation through the electrode to provide local therapy that reduces the inflammatory response at the site of the atherosclerosis and
   to prevent plaque formation and promote stability of existing plaque.

2. The device of claim 1, wherein the device includes an implantable medical device (IMD).

3. The device of claim 1, wherein the device includes a neural stimulator external to a human body.

4. The device of claim 3, wherein the neural stimulator is adapted to deliver therapy transcutaneously.

5. The device of claim 1, wherein the at least one electrode includes an expandable electrode adapted to provide mechanical and electrical anti-atherosclerotic therapy.

6. The device of claim 1, wherein the neural stimulator delivers electrical signals with waveform parameters determined at least in part on sensed arterial blockage levels.

7. A medical device, comprising:
   a sensing circuit to receive sensed signals representative of blood flow in a vessel to determine extent of blockage at a site of atherosclerosis;
   at least one neural stimulation electrode adapted to be placed proximate to the site of atherosclerosis to enable stimulation of the site of atherosclerosis or stimulation of a peripheral neural pathway that is proximate to and that innervates the site of atherosclerosis;
   a neural stimulator adapted to deliver an electrical signal through the at least one electrode to stimulate the site of atherosclerosis or to stimulate the peripheral neural pathway proximate to the site of atherosclerosis to provide local therapy that reduces an inflammatory response at the site of atherosclerosis; and
   a programmed controller to communicate with the sensing circuit, wherein the controller is programmed with a therapy for atherosclerotic plagues to control the neural stimulator to intermittently deliver stimulation through the electrode to provide local therapy that reduces the inflammatory response at the site of atherosclerosis and to prevent plaque formation and promote stability of existing plaque, the controller adapted to control delivery of the electrical signal with waveform parameters modulated based on the determined extent of blockage.

8. The device of claim 7, further comprising:
   a pacing circuit adapted to provide cardiac rhythm management therapy.

9. The device of claim 8, wherein neural stimulation therapy is delivered in conjunction with cardiac rhythm management therapy.

10. The device of claim 8, wherein neural stimulation therapy is delivered in conjunction with cardiac preconditioning therapy.

11. The device of claim 8, wherein neural stimulation therapy is delivered in conjunction with cardiac postconditioning therapy.

12. A system, comprising:
   at least one neural stimulation lead having a proximal portion and a distal portion;
   a plurality of electrodes along the distal portion of the at least one lead, at least one of the plurality of electrodes adapted to be placed proximate to a site of atherosclerosis to enable stimulation of the site of atherosclerosis or stimulation of a peripheral neural pathway that is proximate to and that innervates the site of atherosclerosis; and
   a medical device coupled to the proximal portion of the at least one lead, the medical device including:
      a neural stimulator adapted to deliver an electrical signal through the at least one electrode to stimulate the site of atherosclerosis or to stimulate the peripheral neural pathway proximate to the site of atherosclerosis to provide local therapy that reduces an inflammatory response at the site of atherosclerosis; and
      a programmed controller, wherein the controller is programmed with a therapy for atherosclerotic plagues to control the neural stimulator to intermittently deliver stimulation through the electrode to provide local therapy that reduces the inflammatory response at the site of the atherosclerosis and
to prevent plaque formation and promote stability of existing plaque.

13. The system of claim 12, wherein the at least one lead includes a lead with an expandable portion.

14. The system of claim 13, wherein the lead with the expandable portion is placed in a pulmonary artery in proximity of a high concentration of baroreceptors.

15. The system of claim 12, wherein the at least one lead includes a transvascular lead.

16. The system of claim 15, wherein the transvascular lead is placed proximal to a cardiac fat pad.

17. The system of claim 15, wherein the transvascular lead is placed proximal to an aortic nerve.

18. The system of claim 15, wherein the transvascular lead is placed proximal to a carotid nerve.

19. The system of claim 15, wherein the transvascular lead is placed proximal to a vagus nerve.

20. The system of claim 12, wherein the at least one lead includes an epicardial lead.

21. The system of claim 20, wherein the epicardial lead is placed in a cardiac fat pad.

22. The system of claim 12, wherein the plurality of electrodes includes at least one cuff electrode.

23. The system of claim 22, wherein the cuff electrode is placed around an aortic nerve.

24. The system of claim 22, wherein the cuff electrode is placed around a carotid nerve.

25. The system of claim 22, wherein the cuff electrode is placed around a vagus nerve.

26. The system of claim 12, wherein the medical device includes a pacemaker.

27. A system, comprising:
means for monitoring blood pressure in a vessel to determine extent of blockage; and
means for applying neural stimulation based on the extent of blockage, the stimulation adapted to reduce inflammatory response to a site of atherosclerosis to provide a therapy for atherosclerotic plaques;
wherein the means for applying neural stimulation is adapted to intermittently stimulate a peripheral neural pathway that innervates the site of atherosclerosis to prevent plaque formation and promote stability of existing plaque.

28. The system of claim 27, further comprising:
means for applying cardiac rhythm management therapy.

29. The system of claim 27, further comprising:
means for monitoring blood flow in a vessel to determine extent of blockage.

30. The system of claim 27, wherein the means for applying neural stimulation includes at least one lead.

31. The system of claim 30, wherein the at least one lead is placed in a location known to activate the parasympathetic nervous system.

32. The system of claim 30, wherein the at least one lead is placed in proximity to a site of atherosclerosis.

33. A method, comprising:
monitoring blood flow in a vessel to determine extent of blockage;
placing a neural stimulation lead in proximity to a site of atherosclerosis;
applying neural stimulation using an electrical signal with waveform parameters modulated based on the determined extent of blockage, the stimulation adapted to reduce inflammatory response to the site of atherosclerosis to provide a therapy for atherosclerotic plaques; and
preventing plaque formation and promoting stability of existing plaque by applying neural stimulation including stimulating a peripheral neural pathway that innervates the site of atherosclerosis.

34. The method of claim 33, further comprising:
monitoring blood pressure in a vessel to determine extent of blockage.

35. The method of claim 33, further comprising:
applying cardiac rhythm management therapy in conjunction with neural stimulation therapy.

36. The method of claim 33, further comprising:
applying cardiac preconditioning therapy in conjunction with neural stimulation therapy;
wherein the cardiac preconditioning therapy is applied when the extent of blockage reaches a predefined threshold.

37. The method of claim 33, further comprising:
applying cardiac postconditioning therapy in conjunction with neural stimulation therapy;
wherein the cardiac postconditioning therapy is applied when the extent of blockage reaches a predefined threshold.

38. The method of claim 33, wherein applying neural stimulation includes applying electrical signals proximate a site of atherosclerosis.

39. The method of claim 33, wherein applying neural stimulation includes stimulating an autonomic neural target.

40. A method, comprising:
monitoring blood flow in a vessel to determine extent of blockage;
applying neural stimulation based on the extent of blockage, the stimulation adapted to provide a therapy for atherosclerotic plaques, including reducing inflammatory response to a site of atherosclerosis;
applying cardiac preconditioning therapy in conjunction with neural stimulation therapy; and
wherein the cardiac preconditioning therapy is applied when the extent of blockage reaches a predefined threshold.

41. A method, comprising:
monitoring blood flow in a vessel to determine extent of blockage;
applying neural stimulation based on the extent of blockage, the stimulation adapted to provide a therapy for atherosclerotic plaques, including reducing inflammatory response to a site of atherosclerosis;
applying cardiac postconditioning therapy in conjunction with neural stimulation therapy; and
wherein the cardiac postconditioning therapy is applied when the extent of blockage reaches a predefined threshold.

42. A medical device, comprising:
a sensing circuit to receive sensed signals representative of blood flow in a vessel to determine extent of blockage;
a neural stimulator adapted to deliver an electrical signal through at least one electrode to an autonomic neural target;
a controller to communicate with the sensing circuit and to control the neural stimulator to reduce inflammatory response to a site of atherosclerosis to provide a therapy for atherosclerotic plaques;
a pacing circuit adapted to provide cardiac rhythm management therapy;

wherein the neural stimulator and the at least one electrode cooperate to stimulate a peripheral neural pathway that innervates the site of atherosclerosis; and wherein neural stimulation therapy is delivered in conjunction with cardiac preconditioning therapy.

43. A medical device, comprising:

a sensing circuit to receive sensed signals representative of blood flow in a vessel to determine extent of blockage;

a neural stimulator adapted to deliver an electrical signal through at least one electrode to an autonomic neural target;

a controller to communicate with the sensing circuit and to control the neural stimulator to reduce inflammatory response to a site of atherosclerosis to provide a therapy for atherosclerotic plaques;

a pacing circuit adapted to provide cardiac rhythm management therapy;

wherein the neural stimulator and the at least one electrode cooperate to stimulate a peripheral neural pathway that innervates the site of atherosclerosis; and wherein neural stimulation therapy is delivered in conjunction with cardiac postconditioning therapy.

* * * * *

UNITED STATES PATENT AND TRADEMARK OFFICE
CERTIFICATE OF CORRECTION

PATENT NO. : 7,630,760 B2 Page 1 of 1
APPLICATION NO. : 11/284370
DATED : December 8, 2009
INVENTOR(S) : Libbus et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 449 days.

Signed and Sealed this

Twenty-first Day of December, 2010

David J. Kappos
*Director of the United States Patent and Trademark Office*